United States Patent [19]
Badoz et al.

[11] Patent Number: 5,975,899
[45] Date of Patent: Nov. 2, 1999

[54] DENTAL REAMER

[75] Inventors: Jean-Marie Badoz, Doubs; Paul Calas, Toulouse; Hubert Euvrard, Geneuille; Jean-Marie Vulcain, Vitre, all of France

[73] Assignee: Micro-Mega International Manufactures, Besancon, France

[21] Appl. No.: 08/972,599

[22] Filed: Nov. 18, 1997

[30]  Foreign Application Priority Data

Nov. 20, 1996 [FR] France ................................ 96 14347

[51] Int. Cl.$^6$ .................................................. A61C 5/02
[52] U.S. Cl. .............................................................. 433/102
[58] Field of Search .............................................. 433/102

[56] References Cited

U.S. PATENT DOCUMENTS 5,647,745  7/1997  Badoz ...................................... 433/126

*Primary Examiner*—John J. Wilson
*Attorney, Agent, or Firm*—Weiser and Associates, P.C.

[57]  ABSTRACT

The present invention relates to a dental reamer (2) which tapers right down to its tip (1), of the type including helical slits which, on their sides, have cutting lips for boring out dental canals, in which the characteristics of the cutting conditions are defined by, on the one hand, a cutting angle α determined by the tangent to the cutting edge at the cutting point and the perpendicular to the surface to be cut at this point and, on the other hand, a clearance angle β determined by the plane of the cutting surface and the tangent to the inactive face of the cutting edge, characterized in that the value of the cutting angle α is greater than or equal to zero and that of the clearance angle β is greater than zero.

4 Claims, 2 Drawing Sheets

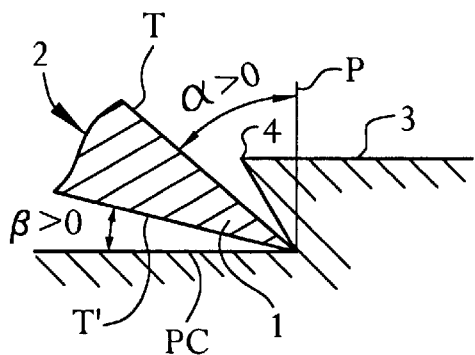
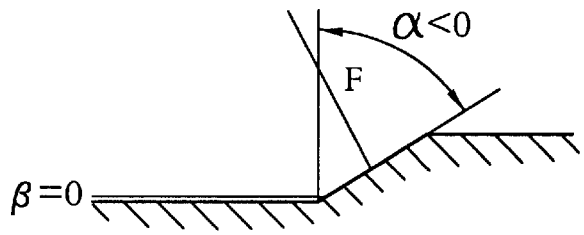
FIG. 1A
FIG. 1B
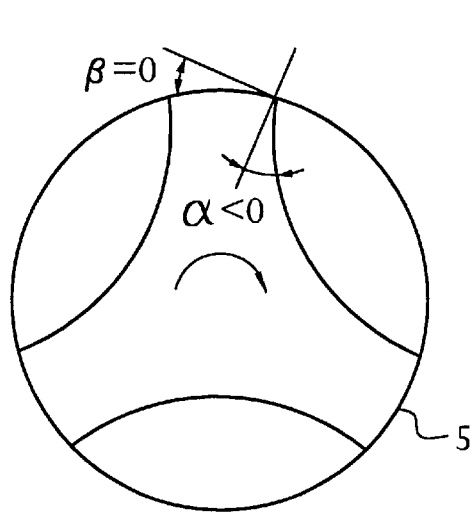
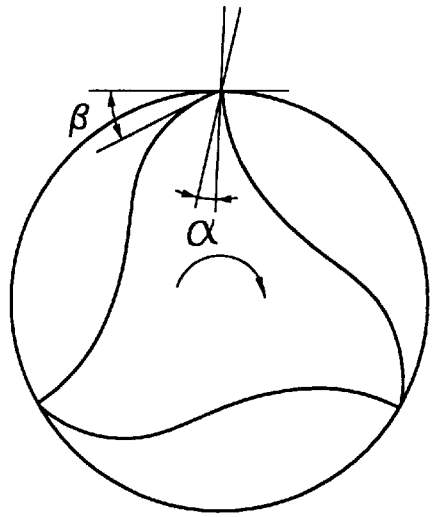
FIG. 2
PRIOR ART
FIG. 3

DENTAL REAMER

BACKGROUND OF THE INVENTION

1. Field of the Invention

The present invention relates to a dental reamer which tapers right down to its tip, of the type including helical slits which, on their sides, have cutting lips for boring out dental canals, in which the characteristics of the cutting conditions are defined by, on the one hand, a cutting angle $\alpha$ determined by the tangent to the cutting edge at the cutting point and the perpendicular to the surface to be cut at this point and, on the other hand, a clearance angle $\beta$ determined by the plane of the cutting surface and the tangent to the inactive face of the cutting edge.

The angles $\alpha$ and $\beta$ will be defined more precisely below.

2. Description of the Related Art

In a boring process using a reamer of the type described above, a compromise must be found between the values of the angles $\alpha$ and $\beta$, which may assume positive or negative values, independently of one another. Depending on the values which are chosen, the results may range from a lack of cutting efficiency, which will need to be compensated for by very strong cutting forces, to a very strong cutting force which will entail a risk of screwing the rotating instrument. As is known, the screwing effect can be eliminated by the presence of a heel on the periphery of the instrument, albeit with the drawback of further increasing the cutting forces and therefore the risk of the instrument being broken.

SUMMARY OF THE INVENTION

The object of the invention is to optimize a reamer structure in which the cutting and clearance angles make it possible to obtain good cutting efficiency while avoiding the screwing effect.

According to the invention, this result is obtained with a reamer of the above type, characterized in that the value of the cutting angle $\alpha$ is greater than or equal to zero and that of the clearance angle $\beta$ is greater than zero.

The cutting edge will preferably be slightly attenuated, so as to obtain a slightly rounded cutting edge, but without thereby compromising the benefit of the cutting angle.

This provides the advantages of guiding the instrument via a small contact surface and optimum cutting efficiency under minimal stress conditions for the instrument, commensurately reducing the risks of breakage.

BRIEF DESCRIPTION OF THE DRAWINGS

Other characteristics of the invention will emerge from the description which is given below with reference to the appended drawings, in which:

FIGS. 1A and 1B schematically illustrate the definition of the cutting and clearance angles, FIG. 2 schematically illustrates a section of a prior art reamer, FIG. 3 schematically illustrates a section of a reamer according to the invention.

DETAILED DESCRIPTION

Reference will first be made to FIGS. 1A and 1B.

The tip (1) of a cutting instrument (2) has been represented schematically. The material to be cut is schematically represented by the section (3) with a step (4).

The cutting angle $\alpha$ is defined by:

the perpendicular P to the cutting plane PC the tangent T to the cutting edge at the cutting point.

The clearance angle $\beta$ is defined by the plane PC and the tangent T' to the inactive face of the cutting edge.

In the representation in FIG. 1A, the values are:

$\alpha > 0$ $\beta > 0$

In the representation in FIG. 1B, the values are:

$\alpha < 0$ $\beta = 0$

In this extreme configuration, with a $\alpha < 0$, the instrument is pushed away. There is no undesirable screwing but there is a considerable loss of efficiency, or even no efficiency at all.

In the representation in FIG. 2, which represents a prior art reamer, the following values are reproduced:

$\alpha < 0$ $\beta = 0$ (or approximately)

The instrument is guided, without screwing, but with low efficiency.

The existence of seals(5) generates are large contact surface, and therefore a high degree of friction. This results in very high resistive moments on the instruments, and therefore high risks of the instruments suffering tension then breakage during an intervention, with all the drawbacks which this may present when working inside a mouth, in order to extract that part of the broken instrument which has remained in the canal.

A reamer according to the invention is represented in cross-section in FIG. 3.

It is in the form of a helix having three branches, in which the values are as follows:

$\alpha \geq 0$ $\beta > 0$

A high cutting efficiency is thus obtained, without friction or screwing as for the representation in FIG. 1A, in approximation. This is reinforced by providing that the working angle of the cutting edge is attenuated or slightly rounded and not sharp.

The benefit of the cutting quality is thus retained while eliminating the risk of screwing and while guiding with a minimum contact surface and therefore low friction.

Figure 4:
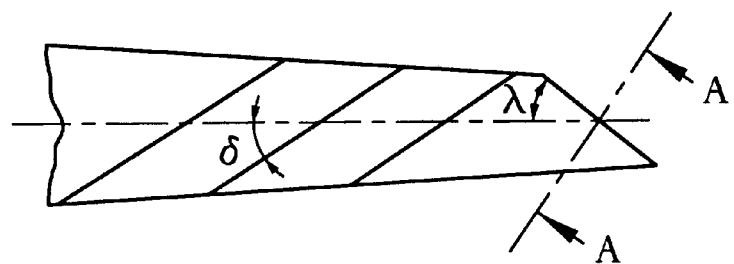
FIG. 4 is an alternative embodiment of the reamer in FIG. 3, at its tip, with various possible cross-sections on A—A which are represented in FIGS. 4A, 4B, 4C 4D.
Figure 4A:
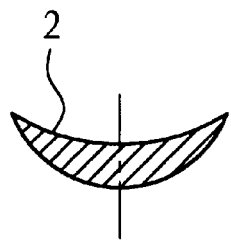
Figure 4B:
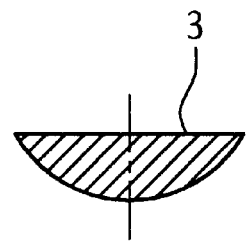
Figure 4C:
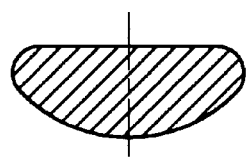
Figure 4D:
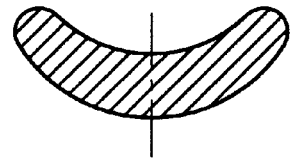

According to an advantageous implementation characteristic, the tips of the reamers (which, for their part, are of conical general shape) will be bevelled so that the bevel plane makes an angle $\lambda$ with the axis of the instrument of opposite direction to the helix angle $\delta$ of the cutting edges, as represented in FIG. 4, with a concave face or a plane face, in order to facilitate the work of practitioners, in particular by preventing erroneous canal formation. This tip geometry makes it possible to increase the cutting capacities of the tip, this being of particular benefit for repeated canal treatment, since the tip becomes very active when it is in contact with the obturation materials put in place previously.

So as to reduce the value of the angle $\beta$, provision may also be made that the tangent to the cutting point of the instrument tends to be superposed with the tangent to the diameter circumscribing a cutting section passing through the said cutting point.

What is claimed is:

1. Dental reamer which tapers right down to its tip having helical slits comprising, on their sides, cutting lips for boring out dental canals, and a plurality of non-linear cutting sides, a plurality of non-linear clearance sides and a plurality of cutting points, wherein the cutting side of a first cutting lip and the clearance side of a second cutting lip form a cutting point having cutting conditions defined by a cutting angle α and a clearance angle β, wherein the cutting angle α, having a value greater than zero, is determined by a tangent to a cutting side at a cutting point and a perpendicular to a tangent to the circumference at the cutting point and wherein the clearance angle β, having a value greater than or equal to zero, is determined by a tangent to the circumference at the cutting point and a tangent to a clearance side at a cutting point, and wherein the cutting lip is slightly attenuated in order to obtain a slightly rounded edge.

2. Dental reamer according to claim 1, comprising a plurality of reamer tips which are beveled, wherein a plane of a bevel makes an angle λ with an axis of the reamer of opposite direction to a helix angle δ of the cutting sides with a concave face or plane face.

3. Dental reamer according to claim 2, wherein the tangent to the cutting point of the reamer tends to be superposed with a perpendicular to a diameter circumscribing a cutting section passing through the cutting point.

4. Dental reamer according to claim 1, wherein the tangent to the cutting point of the reamer tends to be superposed with a perpendicular to a diameter circumscribing a cutting section passing through the cutting point.

* * * * *